United States Patent [19]

Alberts et al.

[11] Patent Number: 4,906,236

[45] Date of Patent: Mar. 6, 1990

[54] SELF-SHEATHING HYPODERMIC NEEDLE

[76] Inventors: David S. Alberts, 250 N. Indian House Rd.; Robert T. Dorr, 1130 Avenida Conalea, both of Tucson, Ariz. 85748

[21] Appl. No.: 237,729

[22] Filed: Aug. 29, 1988

[51] Int. Cl.$^4$ ............................................. A61M 5/32
[52] U.S. Cl. ................................... 604/198; 604/164
[58] Field of Search ............... 604/110, 164, 192, 198, 604/263; 128/764

[56] References Cited

U.S. PATENT DOCUMENTS

| | | | |
|---|---|---|---|
| 3,727,613 | 4/1973 | Sorenson et al. | 604/165 |
| 4,666,435 | 5/1987 | Braginetz | 604/198 |
| 4,775,369 | 10/1988 | Schwartz | 604/263 |
| 4,795,432 | 1/1989 | Karczmer | 604/263 X |
| 4,813,940 | 3/1989 | Parry | 604/198 |
| 4,850,996 | 7/1989 | Cree | 604/198 |

*Primary Examiner*—Dalton L. Truluck
*Attorney, Agent, or Firm*—Cahill, Sutton & Thomas

[57] ABSTRACT

A needle assembly comprises a needle having a sharp point encased within and movable with respect to a sheath having a blunt end. A hub attached to the sheath has a recess therein for receiving a compressible member carried by an end of the needle having a collar thereon for engaging the compressible member. The compressible member retracts the point of the needle into the interior of the sheath to prevent contact of the point by user of the needle. When the needle assembly is attached to a syringe, or other instrument, the collar of the needle is engaged by a portion of the syringe and moved to compress the compressible member and expose the point of the needle for use.

9 Claims, 1 Drawing Sheet

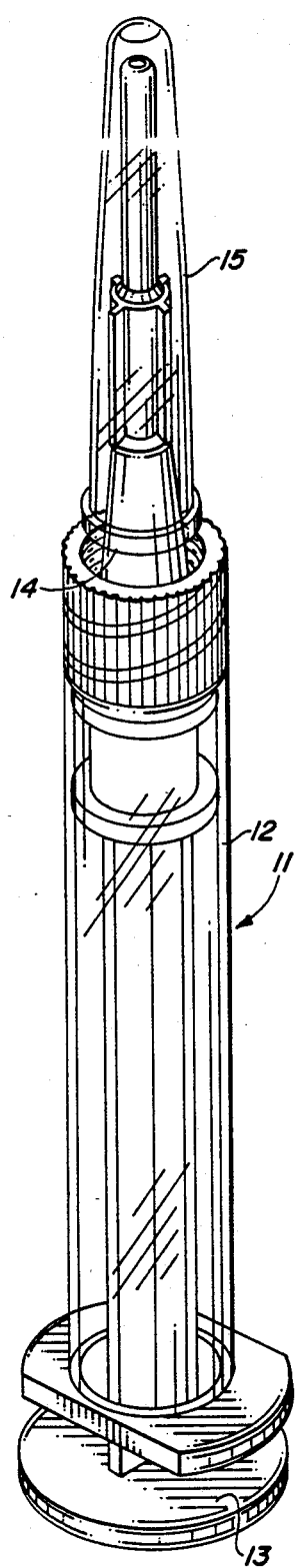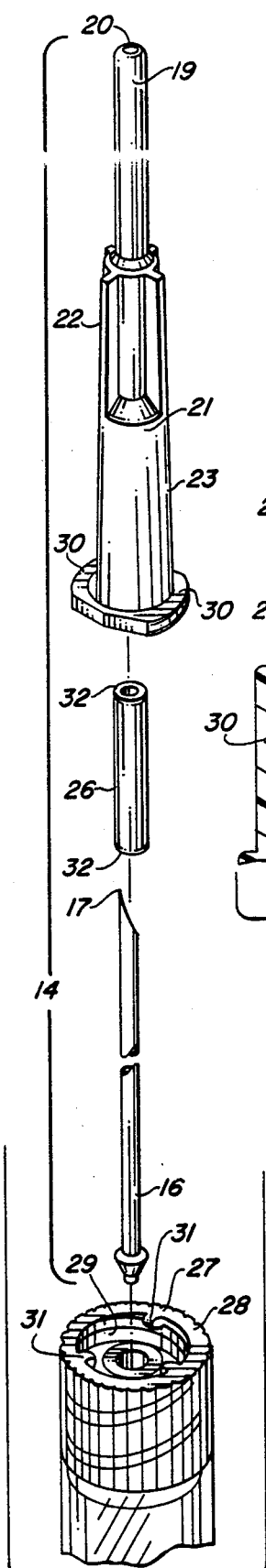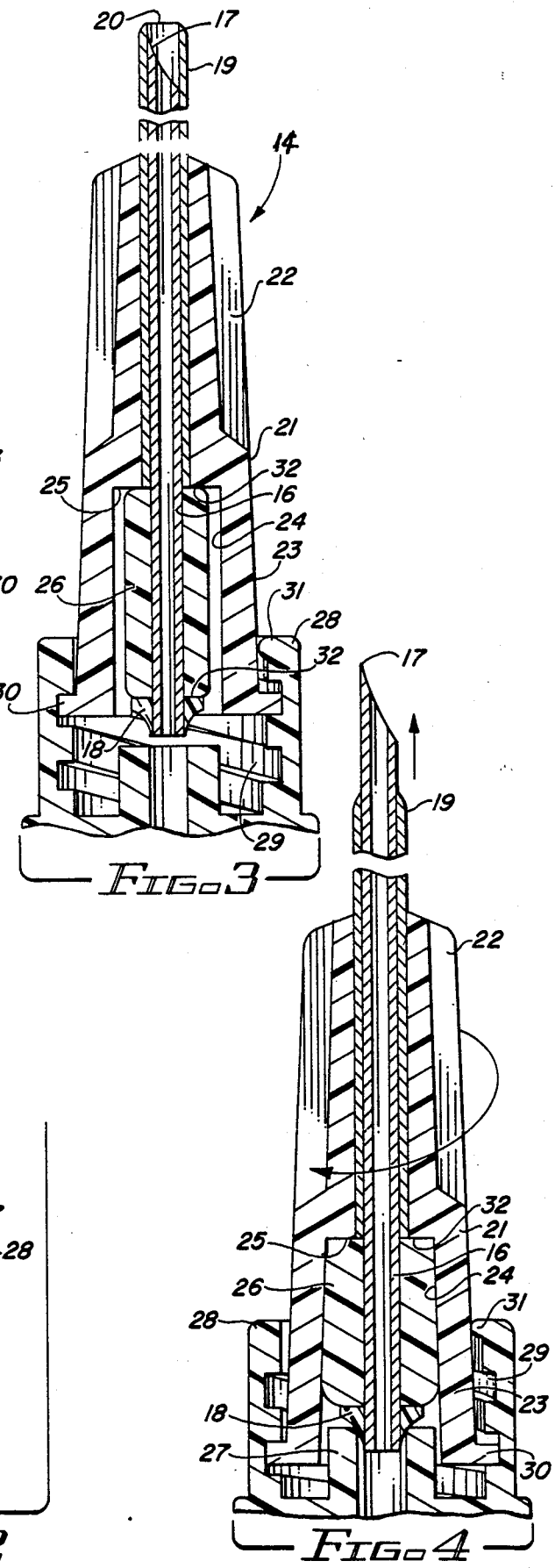
FIG.1  FIG.2  FIG.3  FIG.4

SELF-SHEATHING HYPODERMIC NEEDLE

TECHNICAL FIELD

This invention is concerned with the reduction of needle-stick injuries sustained by health care personnel in handling hypodermic needles.

BACKGROUND ART

Cutaneous punctures by used needles are common occupational injuries for health care personnel. Of particular concern is the risk these workers incur of contracting a systemic disease such as serum hepatitis or acquired immunodeficiency syndrome.

Most needle-stick injuries occur during disposal of used needles, during the administration of parenteral injections or infusion therapy, drawing blood, recapping needles after use, and handling linens or trash containing uncapped needles. The injury risk associated with simply recapping a hypodermic needle after use is sufficiently great for some institutions to discourage their personnel from recapping used needles. See McCormick, R. D., Maki, D. G., Epidemiology of Needle-Stick Injuries in Hospital Personnel, *The American Journal of Medicine*, April, 1981, pgs. 928-932. Of course, the uncapped needles pose serious risks during subsequent handling and disposal, particularly if they are not properly disposed of.

Prior inventors have devised hypodermic syringes with movable covers for the needles. Representative examples of this type syringe are disclosed in U.S. Pat. No. 2,876,770 granted Mar. 10, 1959 to R. A. White for "SHIELDED HYPODERMIC SYRINGE" and U.S. Pat. No. 4,664,654 granted May 12, 1987 to E. C. Strauss for "AUTOMATIC PROTRACTING AND LOCKING HYPODERMIC NEEDLE GUARD". The structures proposed in these patents are fairly complex and, hence, costly and therefore do not lend themselves well to mass produced, disposable syringes which are commonly used today. Moreover, both White and Strauss rely on contact between the needle cover and the epidermis of the patient to force the cover back from the point of the needle as the needle penetrates the epidermis. Such contact between the cover and the epidermis is undesirable and, for certain hypodermic applications, impractical.

A much simpler retractable needle cover is disclosed in U.S. Pat. No. 4,139,009 granted Feb. 13, 1979 to M. Alvarez for "HYPODERMIC NEEDLE ASSEMBLY WITH RETRACTABLE NEEDLE COVER". Again, however, retraction of the cover is effected via contact with the epidermis of the patient.

U.S. Pat. No. 3,306,290 granted Feb. 28, 1967 to H. S. Weltman for "AUTOMATICALLY RETRACTABLE NEEDLE SYRINGE" discloses a syringe having a needle cover. In this syringe the needle moves out from the cover when the syringe plunger is actuated to move a fluid carrying carpule forward within the syringe. The needle remains exposed until the syringe is disassembled.

A somewhat related class of medical instruments includes venipuncture catheters which are used to withdraw blood from or infuse liquids into blood vessels. These are indwelling devices, often made of flexible material, which require a sharp pointed instrument, such as a needle, for initial placement, but which require the needle to be either withdrawn or sheathed after placement to prevent damage to the vascular lumen and associated tissue. Examples of this type of device are disclosed in U.S. Pat. No. 3,506,007 granted Apr. 14, 1970 to M. L Henkin for "CATHETER-NEEDLE"; U.S. Pat. No. 3,727,613 granted Apr. 17, 1973 to J. L. Sorenson et al. for "SAFETY CATHETER PLACEMENT ASSEMBLY"; U.S. Pat. No. 4,713,057 granted Dec. 15, 1987 to J. Huttner et al. for "MECHANICAL ASSIST DEVICE FOR INSERTING CATHETERS"; and U.S. Pat. No. 4,627,841 granted Dec. 9, 1986 to R. T. Dorr for "INFUSION NEEDLE". In each of the devices disclosed in the Henkin, Sorenson et al. and Huttner et al. patents when the needles are removed from the catheters they pose the same serious injury risks as do other unsheathed or uncapped syringe needles.

The Dorr infusion needle is a special purpose device in which a blunt end catheter protrudes from a sharp-tipped hollow needle except when the needle is advanced over the catheter for insertion of the device into a blood vessel. Spring means bias the catheter to its indwelling position in which it protrudes from the needle to prevent damage to the vein or other tissue.

There continues to be a need for a self-sheathing hypodermic needle which can be used with syringes and intravenous instruments. See Jagger, J., Hunt, E. H., Brand-Elnagger, J., Pearson, R. D., Rates of Needle-Stick Injury Caused by Various Devices in a University Hospital, *The New England Journal of Medicine*, Aug. 4, 1988, pgs 284-288.

DISCLOSURE OF THE INVENTION

This invention contemplates a needle assembly in which a sharp-pointed needle is associated with a tubular shield or sheath having a blunt distal end. The needle assembly further includes elastic means which holds the needle and sheath in a position in which the distal end of the sheath projects beyond the point of the needle. When the needle assembly is affixed to a syringe or other holder a portion of the syringe engages the needle and moves the needle relative the sheath and against the action of the elastic member to a position where the point of the needle is exposed. When the connection between the needle assembly and the syringe is loosened the elastic member moves the needle in relation to the sheath so the blunt end of the sheath again projects beyond the point of the needle. If the needle assembly is separated entirely from the syringe the elastic member insures that the blunt end of the sheath projects beyond the point of the needle.

BRIEF DESCRIPTION OF THE DRAWING

The invention is described in greater detail hereinafter by reference to the accompanying drawing wherein:

FIG. 1 is a perspective view of a syringe utilizing the needle assembly of this ivention;

FIG. 2 is an exploded perspective view of the needle assembly;

FIG. 3 is a fragmentary vertical sectional view through the needle assembly illustrating how the needle assembly is connected to a syringe with its needle retracted; and FIG. 4 is a view similar to FIG. 3 but showing the needle of the assembly exposed.

BEST MODES FOR CARRYING OUT THE INVENTION

Referring particularly to FIG. 1, the syringe there illustrated is designated generally by reference numeral 11 and is comprised of a hollow body 12 having a plunger 13 slidably received therein. The syringe 11 is of conventional construction and is preferably molded of a transparent plastic material to permit the contents thereof to be observed. Carried at the forward end of the syringe 11 is a needle assembly designated generally by reference numeral 14 and a cap, or cover, 15 is friction fitted over the needle assembly 14.

In modern practice a disposable syringe 11 will usually be delivered from the manufacturer in a sterile package with the needle assembly 14 and needle cap 15 in place thereon. With a conventional needle in place on syringe 11, once the cap 15 is removed the needle is exposed and capable of inflicting a puncture wound on any part of the body coming in contact therewith. The needle is particularly dangerous after having been used because it then likely has blood or other body fluids thereon from the patient. It is at this stage and during subsequent disposal of the needle that most needle-stick injuries occur. In accordance with this invention needle assembly 14 is constructed so as to significantly reduce the likelihood of the user receiving a needle-stick injury after the cap 15 has been removed.

Referring particularly to FIG. 2 needle assembly 14 comprises an elongated hollow needle 16. Needle 16 is preferably made from a strong metal, such as stainless steel, and has a sharpened point 17 at one end thereof and a collar 18 affixed thereto near the opposite end thereof. Needle 16 is slidingly received in a tubular metal shield, or sheath, 19 having a blunt distal end 20. Sheath 19 has a hub 21 thereon.

Hub 21 is preferably formed of molded plastic material and configured to provide a plurality of flutes 22 on the outer surface thereof providing gripping means for augmenting the purchase one can achieve when gripping the hub between one's thumb and forefinger for the purpose of manipulating the needle assembly 14. Hub 21 further has a cylindrical extension 23 providing a cylindrical recess 24 therein which is coaxial with the needle 16 and the sheath 19.

Disposed on needle 16 within hub extension recess 24 between needle collar 18 and the bottom wall 25 of recess 24 is a compressible elastic member 26. Compressible member 26 is tubular in configuration and may be made from any suitable compressible and sterilizable material, such as natural or synthetic rubber, such as neoprene, or flexible plastic material such as polyethylene. The purpose of compressible member 26 is to position needle 16 within sheath 19 in such a manner that the point 17 of the needle is inside the blunt end 20 of the sheath and therefore inaccessible to the hands or fingers of a user of the needle assembly 14.

It is contemplated that when the needle assembly 14 is attached to a syringe 11 that the compressible member 26 will permit the needle 16 to be moved forward within sheath 19 so as to expose the point 17 of the needle for use in subcutaneous insertion of the needle. The manner in which the needle assembly 14 is manipulated for this purpose is illustrated in FIGS. 3 and 4.

Many syringes 11 in use today have a nozzle 27 protruding from the end of the syringe body 12 and this nozzle is surrounded by a cylindrical mounting flange 28. Flange 28 and sheath hub extension 23 cooperate as threaded connecting means for connecting the needle assembly 14 to the syringe body 12. In the preferred embodiment there illustrated the mounting flange 28 has threads 29 molded into the interior surface thereof which are adapted to be engaged by lugs 30 extending outwardly from the rearmost portion of sheath hub extension 23.

With the end of sheath hub extension 23 inside the mounting flange 28 relative turning motion between the needle assembly 14 and the syringe body 12 moves the lugs 30 in the threads 29 in the mounting flange to cause the needle assembly 14 to draw into or move outwardly of the flange 28. The effect this turning motion the user grasps the flutes 22 on hub 21 between the thumb and forefinger of one hand, grasps the syringe body 12 in the other hand, and twists the needle assembly 14 with respect to the syringe body 12.

When the needle assembly 14 is turned to advance its hub extension 23 into mounting flange 28 the collar 18 on needle 16 engages nozzle 27 protruding from the forward end of the syringe body 12. As the hub extension 23 continues to advance into the mounting flange 29 needle 16 is moved relative to sheath 19 so that its point 17 is exposed beyond the blunt end 20 of the sheath. With the point exposed the syringe is then in condition for use in which the needle 17 enters a subcutaneous region of the patient's body.

Movement of needle 16 to its extended or active position shown in FIG. 4, of course, compresses compressible member 26 between the needle collar 18 and the bottom wall 25 of the recess 24 in hub 21. The energy thus stored in the compressed member 26 is available to retract the needle 16 whenever the needle assembly 14 is rotated within the mounting flange 28 of syringe body 12 to move the needle assembly 14 in a direction away from the end of the syringe body. This is accomplished without having the hand or fingers of the user approach in any way the exposed needle point 17. The fingers of the user remain well behind the point 17 and in a low risk position. This is to be contrasted with the risk associated with replacing a cap 15 over the needle assembly 14 in which the thumb and fingers are required to move in a direction toward and virtually head on with the point 17 of the needle. Of course, with the needle point 17 retracted within sheath 19 there is no necessity for replacing cap 15 as the needle point 17 is no longer a hazard to persons handling the syringe and the needle assembly.

It is desirable to provide the mounting flange 28 with several detent protrusions 31 to prevent the needle assembly 14 from becoming accidentally dislodged from the mounting flange 28 as the needle assembly 14 is turned to retract needle 17. These protrusions 31 can be formed at the entrance to the interior of mounting flange 28. There is sufficient flexibility in the plastic components of mounting flange 28 and lugs 30 on hub extension 23 to permit the lugs 30 to be snapped past the protrusions 31 when the user intends to separate the needle assembly 14 from the syringe body 12.

It is nevertheless desirable that the needle assembly 14 remain intact if it is ever separated from the syringe body 12. This condition can be assured by applying small quantities of adhesive 32 to the ends of compressible member 26 to affix that member to the needle collar 18 and to sheath hub 21.

In the needle assembly described above shield, or sheath, 19 consists of a metal tube. It should be appreciated, however, that the sheath can be molded integrally with and from the same plastic material as hub 21. It will be further apparent to those skilled in the art that shield, or sheath, 19 can be disposed within needle 17 so long as provision is made for relative axial movement of the needle and the shield.

It should also be appreciated that although the needle assembly 14 is described above as used in connection with a syringe it can be used with other holders as well. For example, the benefits of this invention can be utilized in intravenous assemblies, such as a vacuum tube phlebotomy assembly.

From the foregoing it should be apparent that this invention provides a convenient and reliable mechanism for sheathing a hypodermic needle to significantly reduce the possibility of needle-stick injury to users of the needle.

What is claimed is:

1. A combination comprising a needle assembly and a needle holder, said needle assembly comprising a hollow needle having a sharpened points at its distal end, a hollow shield coaxially disposed with respect to said needle, said shield having a blunt distal end, said needle and said shield being relatively axially movable between a first position in which the blunt end of the shield projects beyond the sharpened point of the needle and a second position in which the sharpened point of the needle projects beyond the blunt end of the shield, and means biasing said needle and said shield to said first position, and means for detachably connecting said needle assembly to said needle holder, said last named means comprising means for moving said needle and shield to said second position in response to relative movement between said needle assembly and said holder.

2. The combination recited in claim 1 further characterized in that said biasing means is effective to hold said needle and said shield in said first position when the needle assembly is separated from said holder.

3. The combination recited in claim 1 further characterized in that said needle assembly has gripping means thereon remote from the sharpened point on said needle to facilitate effecting relative movement between said needle assembly and said holder.

4. A needle assembly for use in conjunction with a holder comprising a hollow needle having a sharpened point at its distal end and a collar on the opposite end thereof, a hollow sheath having a blunt distal end, said sheath being disposed on said needle, a hub on said sheath, said hub having an extension thereof providing a recess which is coaxial with said needle and said sheath, and a compressible elastic member positioned in said recesss on said needle in engagement with said needle collar, the arrangement being such that when said member is in an uncompressed condition said needle is positioned with its point inside said sheath and when said member is compressed between said collar and said hub the needle is positioned with its point projecting beyond the blunt distal end of the sheath.

5. A combination comprising the needle assembly of claim 4 and a holder, said holder having a needle assembly mounting flange at one end thereof, said mounting flange and said sheath hub extension comprising threaded connecting means by which the sheath hub extension is advanced into the mounting flange by relative rotation of the hub and the flange, said holder having an portion thereof engagable by said needle collar when the needle assembly is advanced into the mounting flange to compress said member and move the point of the needle outside the sheath.

6. The combination recited in claim 5 further characterized in that said threaded connected means comprises threads on the inside of said mounting flange and at least one lug on said sheath hub extension for engaging said threads.

7. The needle assembly of claim 4 further characterized in that said sheath hub has a fluted surface to facilitate holding the needle assembly between one's fingers.

8. A combination comprising the needle assembly of claim 4 and a syringe constituting said holder, said syringe having a nozzle at one end thereof and a needle assembly mounting flange surrounding said nozzle, said mounting flange and said sheath hub extension comprising threaded connecting means by which the sheath hub extension is advanced into the mounting flange by relative rotation of the hub and the flange, said syringe nozzle being engagable by said needle collar when the needle assembly is advanced into the mounting flange to compress said member and move the point of the needle outside the sheath.

9. The combination recited in claim 8 further characterized in that said threaded connecting means comprises threads on the inside of said mounting flange and at least one lug on said sheath hub extension for engaging said threads.

* * * * *